US010512704B2

(12) United States Patent
Dytioco et al.

(10) Patent No.: US 10,512,704 B2
(45) Date of Patent: Dec. 24, 2019

(54) CLEANLINESS INDICATION SYSTEMS AND METHODS

(71) Applicant: THE BOEING COMPANY, Chicago, IL (US)

(72) Inventors: Rovelyn T. Dytioco, Seattle, WA (US); Jeffrey H. Hunt, Thousand Oaks, CA (US); Karen L. Hills, Seattle, WA (US); Jamie J. Childress, Seattle, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 15/633,869

(22) Filed: Jun. 27, 2017

(65) Prior Publication Data

US 2018/0369440 A1     Dec. 27, 2018

(51) Int. Cl.
*A61L 2/28* (2006.01)
*A61L 2/10* (2006.01)
*B64D 11/02* (2006.01)
*G01N 21/94* (2006.01)
*G01N 21/64* (2006.01)

(52) U.S. Cl.
CPC .................. *A61L 2/28* (2013.01); *A61L 2/10* (2013.01); *B64D 11/02* (2013.01); *G01N 21/94* (2013.01); *A61L 2202/11* (2013.01); *A61L 2202/14* (2013.01); *A61L 2202/25* (2013.01); *G01N 21/6447* (2013.01)

(58) Field of Classification Search
CPC . A61L 2/10; A61L 12/063; A61L 2/28; A47K 13/302; B08B 7/0057

USPC ........................................................ 422/24
See application file for complete search history.

(56) References Cited

U.S. PATENT DOCUMENTS 4,819,276 A     4/1989   Stevens
2001/0048891 A1*   12/2001   McGeorge ................ A61L 2/10
                                                      422/22

(Continued)

FOREIGN PATENT DOCUMENTS

WO     WO 8906347    *   7/1989
WO     WO 2014036217     3/2014

OTHER PUBLICATIONS

Edinburgh Instruments, "What is the Difference between Luminescence, Photoluminescence, Fluorescence, and Phosphorescence," Retrieved from the Internet: [Mar. 11, 2019]; Retrieve from url <https:www.edinst.com/blog/photoluminescence-differences/>. (Year: 2019).*

(Continued)

*Primary Examiner* — Yara B Green
(74) *Attorney, Agent, or Firm* — Joseph M. Butscher; The Small Patent Law Group, LLC (57) ABSTRACT

A cleanliness indication system and a method that indicate that a surface of a component is clean. The cleanliness indication system and method include a photoluminescent indicator that is configured to be on the surface of the component. The photoluminescent indicator is configured to be exposed to ultraviolet (UV) light during a UV light sanitizing cycle. The photoluminescent indicator emits light due to exposure to the UV light. The photoluminescent indicator indicates that the surface of the component is clean by emitting the light due to exposure to the UV light.

20 Claims, 5 Drawing Sheets

(56) References Cited

U.S. PATENT DOCUMENTS

| | | | |
|---|---|---|---|
| 2004/0211917 A1* | 10/2004 | Adamovics | G01T 1/06 |
| | | | 250/474.1 |
| 2006/0223731 A1* | 10/2006 | Carling | A61L 2/18 |
| | | | 510/156 |
| 2007/0231188 A1 | 10/2007 | Jung | |
| 2014/0059796 A1* | 3/2014 | Boodaghians | A61L 2/10 |
| | | | 15/339 |
| 2014/0115764 A1 | 5/2014 | Cheng | |
| 2015/0137747 A1* | 5/2015 | Salter | A61L 2/10 |
| | | | 320/108 |
| 2016/0247381 A1* | 8/2016 | Rensvold | G16H 40/20 |
| 2017/0008074 A1 | 3/2017 | Young | |

OTHER PUBLICATIONS

Extended European Search Report for EP 18176627.0-1104, dated Nov. 22, 2018.

* cited by examiner

CLEANLINESS INDICATION SYSTEMS AND METHODS

FIELD OF THE DISCLOSURE

Embodiments of the present disclosure generally relate to cleanliness indication systems and methods, and, more particularly, to systems and methods of indicating that particular surfaces have been sanitized with ultraviolet light.

BACKGROUND OF THE DISCLOSURE

Commercial aircraft are used to transport passengers between various locations. A typical commercial aircraft includes one or more lavatories within an internal cabin.

Systems are currently being developed to disinfect or otherwise sanitize surfaces within aircraft lavatories that use ultraviolet (UV) light. For example, it has been found that far UV light efficiently disinfects exposed surfaces within a lavatory.

A UV light sanitizing system emits UV light onto a surface to be sanitized within an unoccupied lavatory. That is, the UV light sanitizing process occurs when no one is in the lavatory. Therefore, when an individual enters the lavatory after the UV light sanitizing process, the individual may not be aware that certain surfaces within the lavatory have been sanitized between uses.

SUMMARY OF THE DISCLOSURE

A need exists for a system and method that indicate that surfaces within a lavatory have been sanitized and are clean. Further, a need exists for a system and method that allow individuals to rest assured that surfaces within a lavatory, for example, are clean and sanitary.

With those needs in mind, certain embodiments of the present disclosure provide a cleanliness indication system that is configured to indicate that a surface of a component is clean. The cleanliness indication system includes a photoluminescent indicator that is configured to be on the surface of the component. The photoluminescent indicator is configured to be exposed to ultraviolet (UV) light during a UV light sanitizing cycle. The photoluminescent indicator emits light due to exposure to the UV light. The photoluminescent indicator indicates that the surface of the component is clean by emitting the light due to exposure to the UV light.

The photoluminescent indicator emits the light for a predefined period of time after being exposed to the UV light. The photoluminescent indicator does not emit the light in the absence of being exposed to the UV light. The photoluminescent indicator may be configured to emit a visible light after being exposed to a threshold level of UV light energy.

The photoluminescent indicator may be mounted onto the surface of the component. The photoluminescent indicator may form at least a portion of the component.

The cleanliness indicator system may also include a transparent cover positioned over the photoluminescent indicator. The cleanliness indicator system may also include a light filter positioned over the photoluminescent indicator.

In at least one embodiment, the photoluminescent indicator includes a strip or block of photoluminescent material having a particular shape. In at least one embodiment, the photoluminescent indicator is formed as text. In at least one embodiment, the photoluminescent indicator is formed as a graphic. In at least one embodiment, the photoluminescent indicator is formed as an advertisement.

Certain embodiments of the present disclosure provide a cleanliness indication method that is configured to indicate that a surface of a component is clean. The cleanliness indication method includes disposing a photoluminescent indicator on the surface of the component, exposing the photoluminescent indicator to ultraviolet (UV) light during a UV light sanitizing cycle, emitting light from the photoluminescent indicator due the exposing, and indicating that the surface of the component is clean by the emitting.

Certain embodiments of the present disclosure provide a vehicle including an internal cabin, and a lavatory within the internal cabin. The lavatory includes a floor that supports a toilet and a sink. At least on ultraviolet (UV) light source is configured to emit UV light onto at least one surface of the floor, the toilet, or the sink during a UV light sanitizing cycle. A cleanliness indication system is configured to indicate that the surface(s) of the floor, the toilet or the sink is clean. The cleanliness indication system includes at least one photoluminescent indicator on the surface(s). The photoluminescent indicator(s) is exposed to the UV light during the UV light sanitizing cycle. The photoluminescent indicator(s) emits light due to exposure to the UV light. The photoluminescent indicator(s) indicates that the surface(s) is clean by emitting the light due to exposure to the UV light.

DETAILED DESCRIPTION OF THE DISCLOSURE

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps.

Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular condition may include additional elements not having that condition.

Certain embodiments of the present disclosure provide a cleanliness indication system that is configured to indicate that a surface of a component has been sanitized, and is therefore clean and ready for use. The cleanliness indication system includes a photoluminescent indicator that emits light (for example, glows) after being exposed to ultraviolet (UV) light that sanitizes the surface of the component. The photoluminescent indicator is configured to glow for a predefined period of time, such as one to three minutes, after exposure to the UV light. In at least one embodiment, the photoluminescent indicator may glow for a predefined period of time after exposure to UV light of one second or less. Further, the degree to which the photoluminescent indicator glows may vary depending on the intensity of the UV light emitted thereon.

Photoluminescence is light emission from a particular material after the material absorbs radiation. Photoluminescence is initiated by photoexcitation. After photoexcitation, relaxation processes occur in which other photons are re-radiated.

Embodiments of the present disclosure provide cleanliness indication systems and methods that allow individuals to know that components have been effectively cleaned between uses, such as via UV light, even though the individuals did not observe the UV light sanitizing process. The cleanliness indication systems and methods do not require electrical power to provide a noticeable indication of cleanliness. Further, the cleanliness indication systems and methods are low-cost, lightweight and do not require electrical power that may be used for other components.

In at least one embodiment, a photoluminescent indicator emits a glowing pattern that conveys to individuals that a surface of a component within a lavatory, for example, has been sanitized via UV light. As such, the individuals can rest assured that they can safely use the lavatory. In at least one embodiment, the photoluminescent indicator may be calibrated to coincide with a particular level of microbe elimination effectiveness. That is, the photoluminescent indicator may be configured to glow after exposure to UV light that is configured to eliminate microbes, germs, and the like.

In at least one embodiment, a surface of interest is periodically exposed to far UV light. The surface of interest is at least partially defined by a photoluminescent material that glows after recent exposure to the far UV light. The surface of interest is one that comes in contact with humans, such as those within a lavatory (for example, countertops, sinks, toilet seats, fixtures, doors, knobs, handles, floors, and/or the like). Other examples of the surface of interest include gloves, a keyboard, a touchpad, a handheld device (such as a smart phone), a toothbrush, and/or the like. The photoluminescent material is not visible in the absence of recent exposure to the far UV light. The photoluminescent material is arranged in a pattern that conveys a message to individuals. For example, the pattern may convey an indication that the surface is clean. In at least one embodiment, the pattern may also convey an advertisement.

Figure 1:
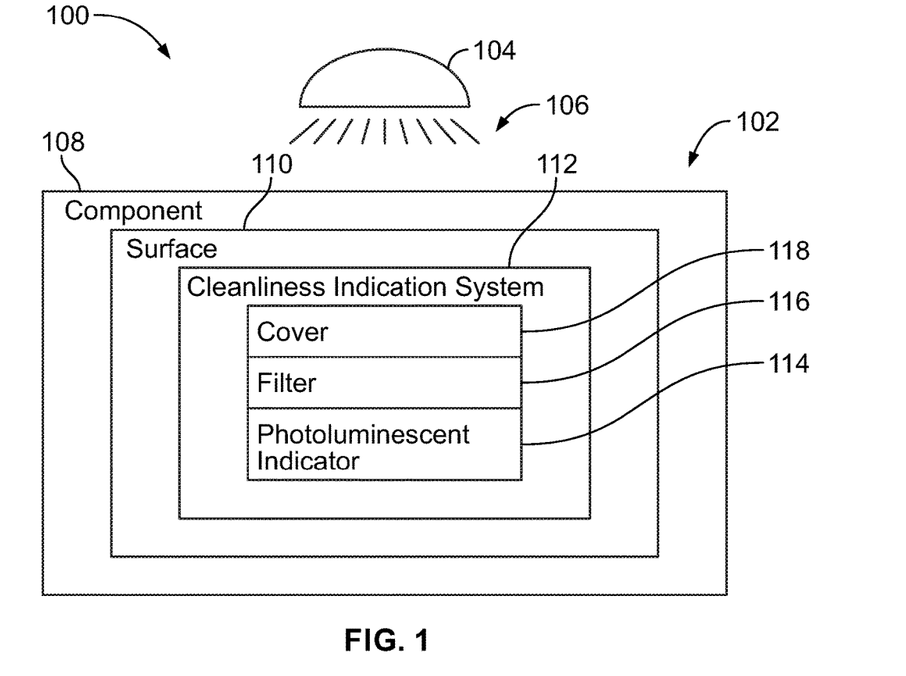
FIG. 1 illustrates a schematic diagram of an ultraviolet light sanitizing system for an enclosed space, according to an embodiment of the present disclosure.

FIG. 1 illustrates a schematic diagram of an ultraviolet (UV) light sanitizing system 100 for an enclosed space 102, according to an embodiment of the present disclosure. The UV light sanitizing system 100 includes a UV light source 104 that sanitizes a component 108 by emitting sanitizing UV light onto a surface 110 of the component 108.

In at least one embodiment, the enclosed space 102 is a lavatory, such as onboard a vehicle. Examples of the component 108 include a toilet, a countertop, a sink, a faucet, a floor, a wall, or the like. In at least one other embodiment, the enclosed space 102 is a food preparation area, such as a galley, kitchen, medical environment (such as a hospital room, operating room, or the like). In this embodiment, examples of the component 108 include a food preparation table, an oven, a sink, a faucet, and/or the like. Other examples of the component 108 include an examination table, an operating table, and medical devices, equipment, implements, and the like.

The surface 110 may be one that is contacted by individuals. For example, the surface 110 may be a countertop, a sink, a toilet seat, a fixture, a door, a door knob, a handle, a portion of a floor, and/or the like.

The light source 104 includes one or more UV light elements, such as an arc lamp(s), laser(s), light emitting diode(s) (LEDs), microfilament(s), fiber optic element(s), bulb(s), and/or the like. In at least one embodiment, the light source 104 emits the UV light 106 as far UV light that is used to sanitize the surface 110 of the component 108. Alternatively, the UV light 106 may be UVA light, UVB light, UVC light, vacuum UV light, or the like. In at least one embodiment, the light source 104 may include UV light elements that are configured to emit UV light with different UV bands (for example, at different wavelengths and different frequencies). For example, one UV light element may be configured to emit far UV light, while another UV light element may be configured to emit UVC light.

The surface 110 is an exposed portion of the component that receives the UV light 106 during a sanitizing process, such as a sanitizing cycle. The surface 110 includes a cleanliness indication system 112. For example, the cleanliness indication system 112 may be securely mounted onto the surface 110, such as through one or more fasteners, adhesives, and/or the like. In at least one embodiment, the cleanliness indication system 112 is integrally formed with the surface 110, or proximate to the surface 110. As an example, the cleanliness indication system 112 forms at least a part of the surface 110. In at least one embodiment, the cleanliness indication system 112 may form an entirety of the surface 110. For example, the cleanliness indication system 112 may provide a countertop within a lavatory.

The cleanliness indication system 112 includes a photoluminescent indicator 114 underneath a light filter 116 and a cover 118. The photoluminescent indicator 114 is formed of a photoluminescent material that emits light (for example, glows) after being exposed to the UV light 106. The photoluminescent indicator 114 glows for a predefined period of time after being exposed to the UV light 106. For example, the photoluminescent indicator 114 glows for one to three minutes after being exposed to the UV light 106. Optionally, the photoluminescent indicator 114 may glow for less than one minute, or longer than three minutes after being exposed to the UV light 106.

In at least one embodiment, the photoluminescent indicator 114 is formed of a material that emits light after being exposed to UV light, such as far UV light. The photoluminescent indicator 114 does not need to be coupled to a source of electrical power in order to glow. Instead, the photoluminescent indicator 114 glows due to exposure to the UV light 106.

The filter 116 is secured over the photoluminescent indicator 114. As such, the filter 116 is disposed between the UV light source 104 and the photoluminescent indicator 114. The filter 116 is configured to allow passage of the certain wavelengths of light, such as the UV light. The UV light 106 passes through the filter 116 to excite the photoluminescent indicator 114, but may block other types of light. In this manner, the photoluminescent indicator 114 may only glow after being exposed to the sanitizing UV light 106. In at least one embodiment, the filter 116 may be configured to calibrate the photoluminescent indicator 114 to glow after exposure to UV light that is configured to eliminate microbes, germs, and the like. Optionally, the cleanliness indication system 112 may not include the filter 114.

The cover 118 is secured over the photoluminescent indicator 114. The cover 118 is disposed between the UV light source 104 and the photoluminescent indicator 114. The cover 116 may be disposed over the filter 116. In at least one other embodiment, the filter 116 is disposed over the cover 118. In at least one other embodiment, the filter 116 is formed as part of the cover 118. For example, the filter 116 may be embedded within the cover 118. The cover 118 is formed of a transparent material that allows light to pass therethrough. For example, the cover 118 may be formed of quartz glass, silica glass, or the like. The cover 118 protects the photoluminescent indicator 114 from damage and normal wear and tear. Optionally, the cleanliness indication system 112 may not include the cover 118.

The photoluminescent indicator 114 may be a base of photoluminescent material underneath the cover 118 and/or the filter 116. For example, the photoluminescent indicator 114 may be a strip of photoluminescent material affixed to the surface 110. In at least one other embodiment, the photoluminescent indicator 114 may form at least part of the surface 110 itself. In at least one other embodiment, the photoluminescent indicator 114 may be a layer of photoluminescent material (such as a paint or adhesive) that is applied to an underside of the cover 118 and/or the filter 116.

The photoluminescent indicator 114 may be formed as a particular shape, graphic, text, or the like. For example, the photoluminescent indicator 114 may be formed as text such as "CLEAN," "SANITIZED," or the like. In at least one other embodiment, the photoluminescent indicator 114 may be formed as a graphic, such as a company trademark. In at least one other embodiment, the photoluminescent indicator 114 may be formed as an advertisement, such as "FLY BOEING."

In operation, the UV light source 104 emits the UV light 106 onto the surface 110 to sanitize the surface 102 between uses. For example, after an individual exits a lavatory, the UV light source 104 emits the UV light 106 onto the surface 110 when no one is in the lavatory for a predefined sanitizing period. After the sanitizing period ends (such as after two or three seconds of far UV light exposure), the photoluminescent indicator 114 emits light (for example, glows) due to the exposure to the UV light 106. The glowing photoluminescent indicator 114 provides notification that the surface 110 of the component 108 has been sanitized with UV light 106.

Figure 2:
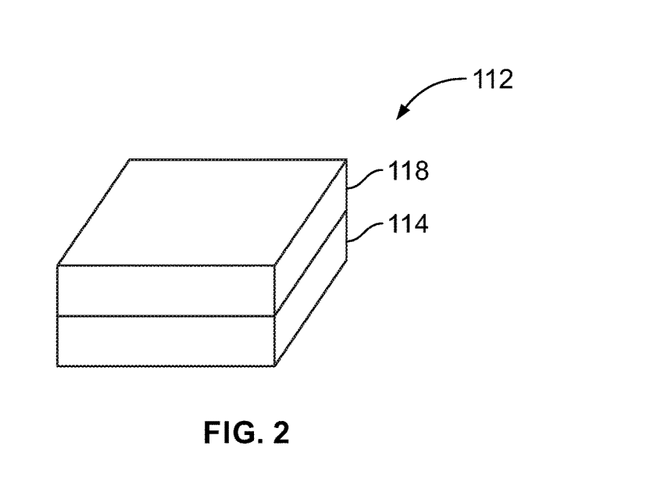
FIG. 2 illustrates a perspective top view of a cleanliness indication system, according to an embodiment of the present disclosure.

FIG. 2 illustrates a perspective top view of a cleanliness indication system 112, according to an embodiment of the present disclosure. As shown, the photoluminescent indicator 114 may be a block of material having a particular shape. For example, the photoluminescent indicator 114 may be formed as a square. In other embodiments, the photoluminescent indicator 114 may be shaped as a circle, triangle, parallelogram, an irregular shape, or the like. The photoluminescent indicator 114 is secured underneath the cover 118. The cleanliness indication system 112 may also include the filter 116 (shown in FIG. 1).

Figure 3:
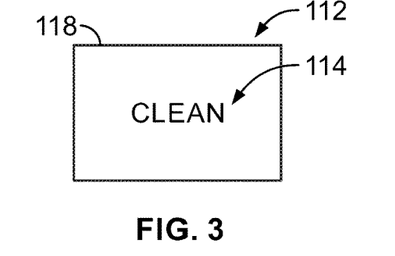
FIG. 3 illustrates a top view of a cleanliness indication system, according to an embodiment of the present disclosure.

FIG. 3 illustrates a top view of a cleanliness indication system 112, according to an embodiment of the present disclosure. In this embodiment, the photoluminescent indicator 114 is formed as text, such as the word "CLEAN." After being exposed to the UV light 106 (shown in FIG. 1), the photoluminescent indicator 114 noticeably glows as the word "CLEAN." Optionally, various other text can be used, such as "SANITIZED," "CLEANED FOR YOUR SAFETY AND COMFORT," and/or the like.

Figure 4:
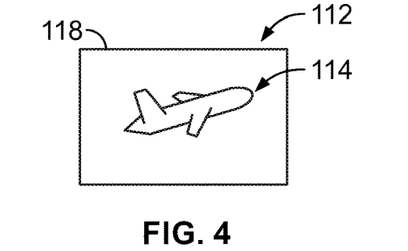
FIG. 4 illustrates a top view of a cleanliness indication system, according to an embodiment of the present disclosure.

FIG. 4 illustrates a top view of a cleanliness indication system 112, according to an embodiment of the present disclosure. In this embodiment, the photoluminescent indicator 114 is formed as a graphic, such as that of an aircraft. Other examples of the graphic include those symbolizing cleanliness (such as a sparkle graphic).

Figure 5:
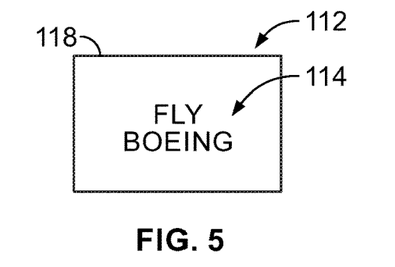
FIG. 5 illustrates a top view of a cleanliness indication system, according to an embodiment of the present disclosure.

FIG. 5 illustrates a top view of a cleanliness indication system 112, according to an embodiment of the present disclosure. In this embodiment, the photoluminescent indicator 114 is formed as an advertisement, which provides a dual function of indicating cleanliness and advertising when glowing after exposure to the UV light 106.

In at least one embodiment, the photoluminescent indicator 114, when illuminated, may be detected by a light-detecting sensor. The illumination of the photoluminescent indicator 114 may be automatically detected in order to provide a feedback loop to a UV sanitizing system. The UV sanitizing system may automatically initiate another sanitizing cycle if the light-detecting sensor does not detect emitted light from the photoluminescent indicator 114.

Referring to FIG. 1-5, the cleanliness indication systems 112 may be secured to the surface 110 of the component 108. In at least one embodiment, the cleanliness indication systems 112 form an integral part of the component 108 (in contrast to being separately affixed the component 108). The photoluminescent indicators 114 are arranged (such as in a shaped pattern, a pattern of text, a graphic(s), and/or the like) to convey a message to an individual.

The photoluminescent indicator 114 emits light (for example, glows) after recent exposure to the UV light 106. For example, the photoluminescent indicator 114 emits light for a period of one minute to three minutes after being exposed to the UV light 106. In the absence of the recent exposure to the UV light 106, the photoluminescent indicator 114 does not emit light. For example, after five minutes from being exposed to the UV light 106, the photoluminescent indicator 114 no longer emits light, and/or is not visible.

Figure 6:
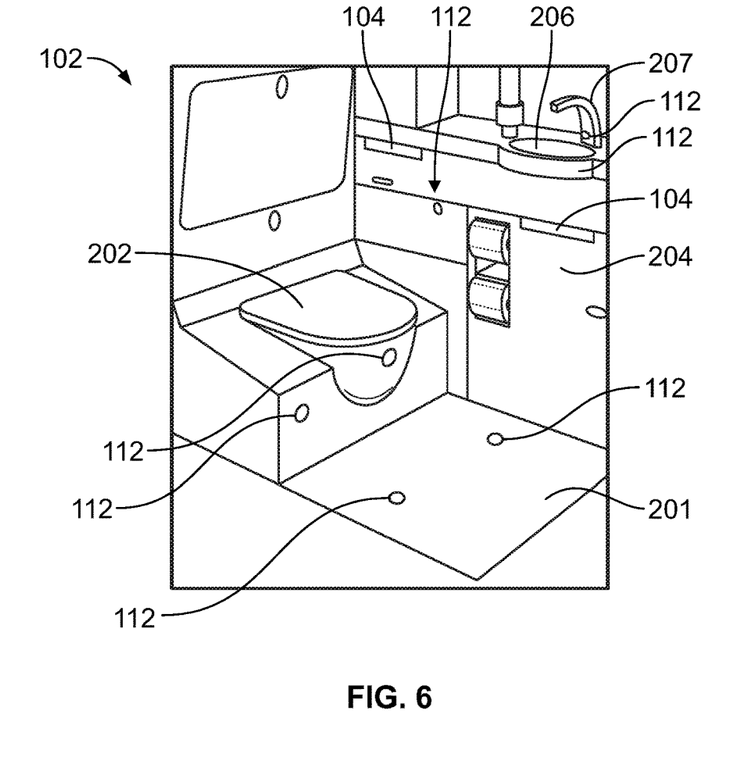
FIG. 6 illustrates a perspective internal view of a lavatory, according to an embodiment of the present disclosure.

FIG. 6 illustrates a perspective internal view of a lavatory 102, according to an embodiment of the present disclosure. The lavatory 102 is an example of the enclosed space 102 shown and described with respect to FIG. 1. The lavatory 102 may be onboard an aircraft. Optionally, the lavatory 102 may be onboard various other vehicles. In other embodiments, the lavatory 102 may be within a fixed structure, such as a commercial or residential building.

The lavatory 102 includes a floor 201 that supports a toilet 202, cabinets 204, and a sink 206. One or more UV light sources 104 are secured within the lavatory 102 and are configured to be activated during a sanitizing cycle to sanitize (for example, disinfect, sterilize, or otherwise clean) various structures within the lavatory 102, such as the toilet 202, the floor 201, the cabinets 204, and/or the sink 206.

Cleanliness indication systems 112 may be secured to, or otherwise form, surfaces of various components within the lavatory 102. For example, the toilet 202 may include a cleanliness indication system 112. One or more cleanliness indication systems 112 may be on the floor 201. The sink 206 may include a cleanliness indication system 112. A cleanliness indication system 112 may be on a portion of the faucet 207. One or more cabinets 204 may include a cleanliness indication system 112. The lavatory 102 may include more or less cleanliness indication systems 112 than shown.

Figure 7:
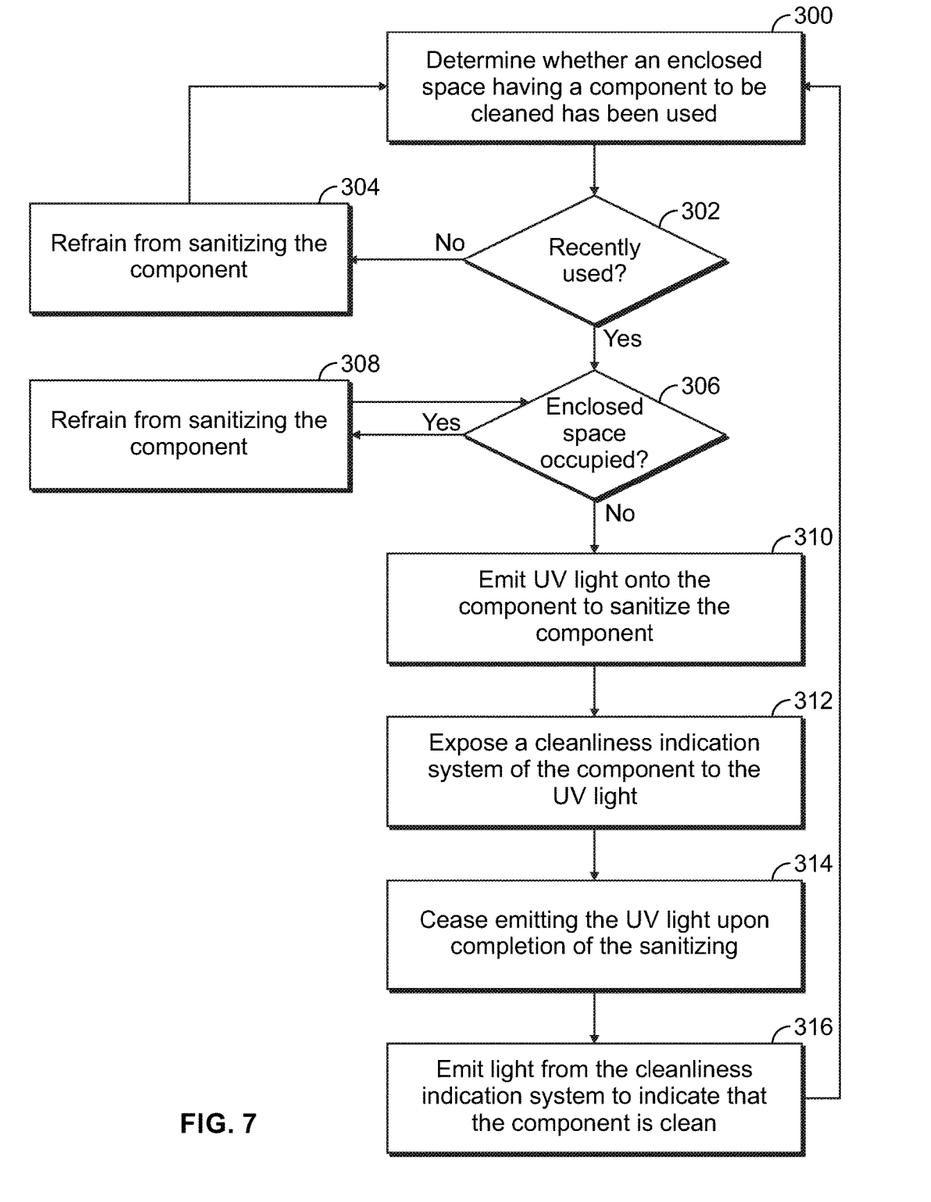
FIG. 7 illustrates a flow chart of a cleanliness indication method, according to an embodiment of the present disclosure.

FIG. 7 illustrates a flow chart of a cleanliness indication method, according to an embodiment of the present disclosure. The method begins at 300, at which it is determined whether an enclosed space having a component to be cleaned has been used. At 302, if the enclosed space has not been recently used, the method proceeds to 304, at which a sanitizing cycle for the component is not initiated, and the method returns to 300.

If, however, the enclosed space has been recently used at 302, the method proceeds to 306, at which it is determined if the enclosed space is currently occupied by an individual. If the enclosed space is occupied, the method proceeds to 308, at which the sanitizing cycle is not initiated, and the method then returns to 306.

If, however, the enclosed space is not occupied, the method proceeds from 306 to 310, at which UV light is emitted onto the component in order to sanitize the component. At 312, a cleanliness indication system of the component (for example, an integral part of the component, or affixed to the component) is exposed to the UV light. At 314, the UV light ceases to be emitted upon completion of the sanitizing cycle. At 316, the cleanliness indication system emits light (due to excitation causes by exposure to the UV light) to indicate that the component is clean. The method then returns to 300.

Figure 8:
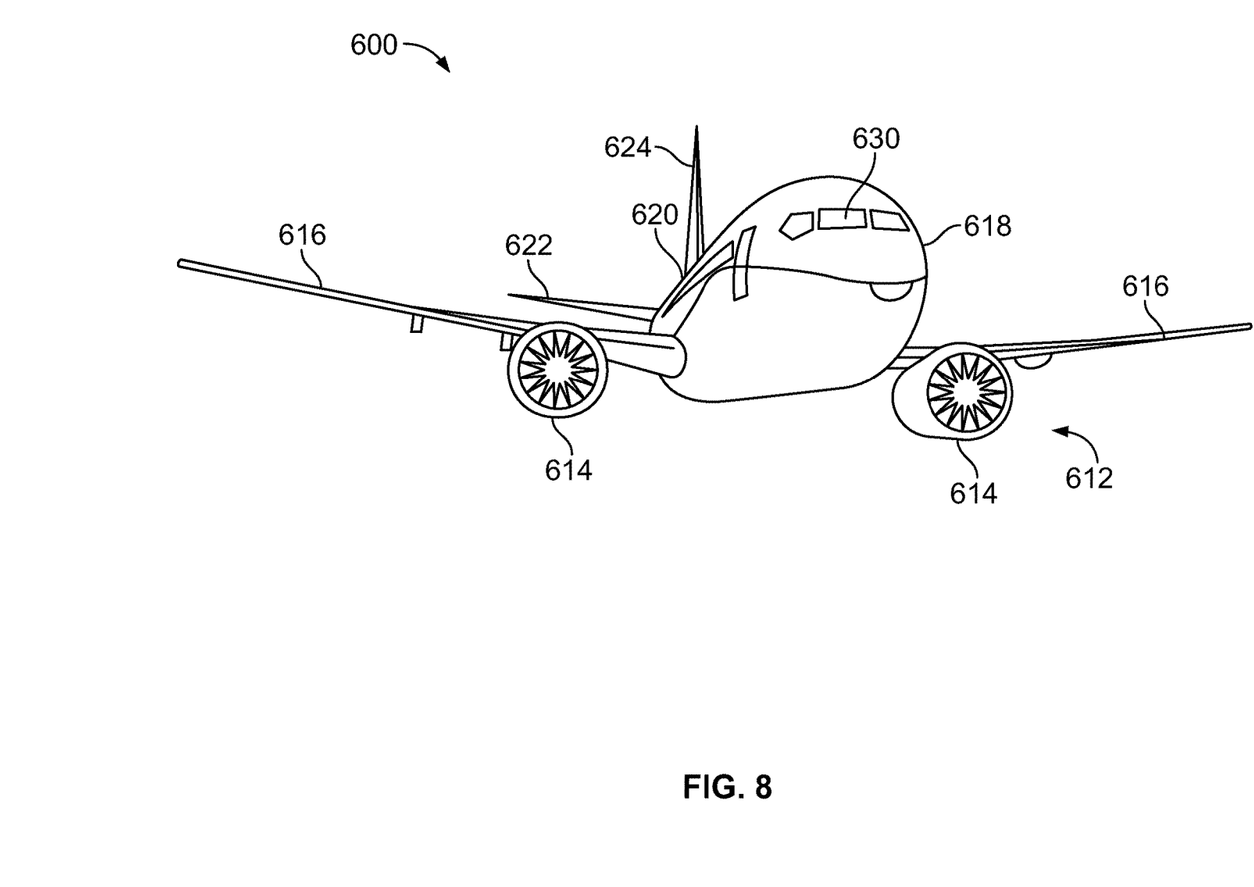
FIG. 8 illustrates a perspective front view of an aircraft, according to an embodiment of the present disclosure.

FIG. 8 illustrates a perspective front view of an aircraft 600, according to an embodiment of the present disclosure. The aircraft 600 includes a propulsion system 612 that may include two turbofan engines 614, for example. Optionally, the propulsion system 612 may include more engines 614 than shown. The engines 614 are carried by wings 616 of the aircraft 600. In other embodiments, the engines 614 may be carried by a fuselage 618 and/or an empennage 620. The empennage 620 may also support horizontal stabilizers 622 and a vertical stabilizer 624.

The fuselage 618 of the aircraft 600 defines an internal cabin, which may include a cockpit, one or more work sections (for example, galleys, personnel carry-on baggage areas, and the like), one or more passenger sections (for example, first class, business class, and coach sections), and an aft section in which an aft rest area assembly may be positioned. Each of the sections may be separated by a cabin transition area, which may include one or more class divider assemblies. Overhead stowage bin assemblies may be positioned throughout the internal cabin. The internal cabin includes one or more chambers, such as lavatories, for example. One or more UV light sanitizing systems 100 (shown and described with respect to FIG. 1) may be located within the internal cabin.

Alternatively, instead of an aircraft, embodiments of the present disclosure may be used with various other vehicles, such as automobiles, buses, locomotives and train cars, watercraft, and the like. Further, embodiments of the present disclosure may be used with respect to fixed structures, such as commercial and residential buildings.

Figure 9:
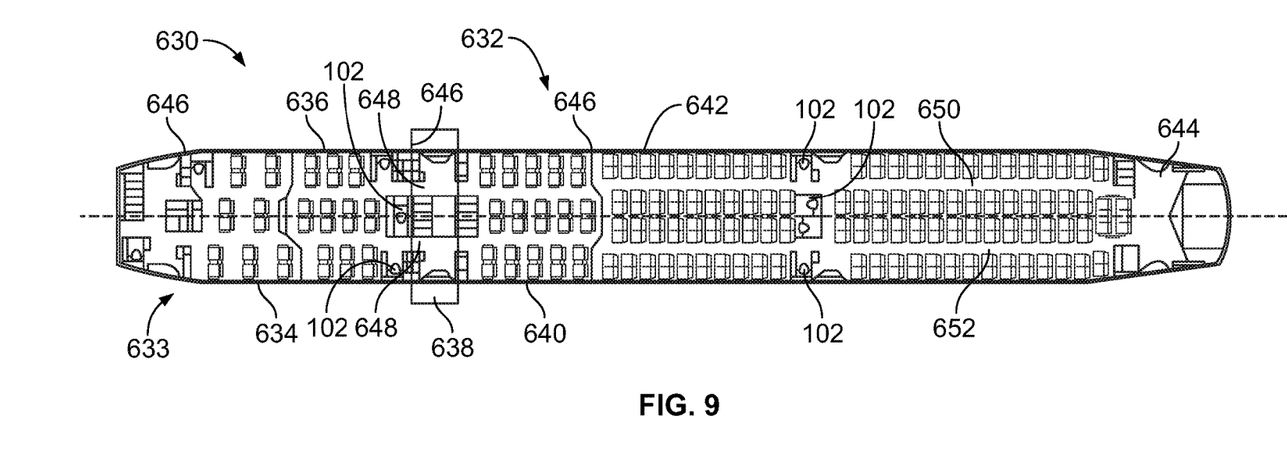
FIG. 9 illustrates a top plan view of an internal cabin of an aircraft, according to an embodiment of the present disclosure.

FIG. 9 illustrates a top plan view of an internal cabin 630 of an aircraft, according to an embodiment of the present disclosure. The internal cabin 630 may be within a fuselage 632 of the aircraft. For example, one or more fuselage walls may define the internal cabin 630. The internal cabin 630 includes multiple sections, including a front section 633, a first class section 634 (or first class suites, cabins, for example), a business class section 636, a front galley station 638, an expanded economy or coach section 640, a standard economy or coach section 642, and an aft section 644, which may include multiple enclosed spaces or chambers 102, such as lavatories and galley stations. It is to be understood that the internal cabin 630 may include more or less sections than shown. For example, the internal cabin 630 may not include a first class section, and may include more or less galley stations than shown. Each of the sections may be separated by a cabin transition area 646, which may include class divider assemblies between aisles 648.

As shown in FIG. 9, the internal cabin 630 includes two aisles 650 and 652 that lead to the aft section 644. Optionally, the internal cabin 630 may have less or more aisles than shown. For example, the internal cabin 630 may include a single aisle that extends through the center of the internal cabin 630 that leads to the aft section 644.

One or more enclosed spaces 102, such as lavatories, may be located within the internal cabin 630. UV light sanitizing systems may be used to sanitize structures within the lavatories 102, such as described above.

Figure 10:
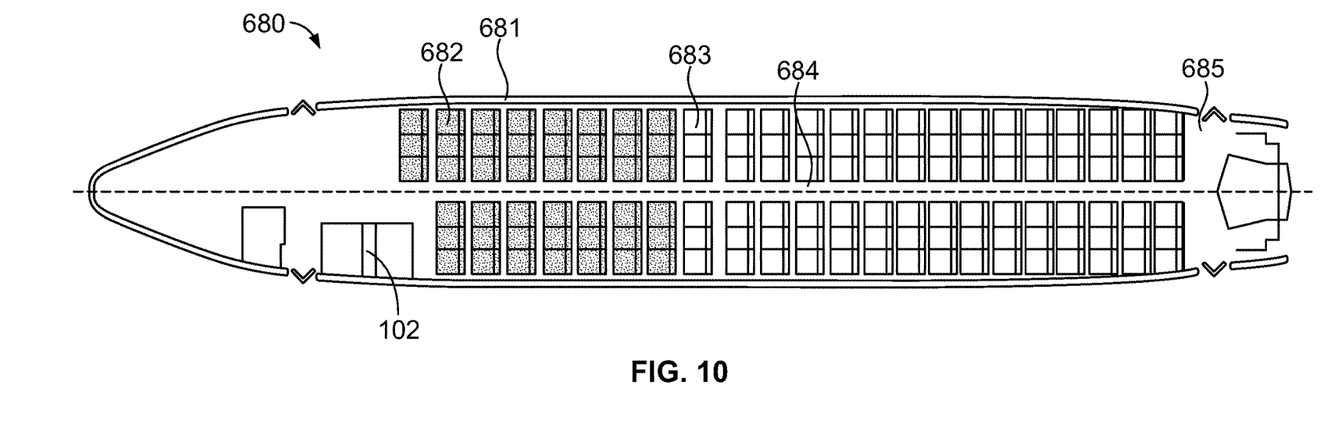
FIG. 10 illustrates a top plan view of an internal cabin of an aircraft, according to an embodiment of the present disclosure.

FIG. 10 illustrates a top plan view of an internal cabin 680 of an aircraft, according to an embodiment of the present disclosure. The internal cabin 680 may be within a fuselage 681 of the aircraft. For example, one or more fuselage walls may define the internal cabin 680. The internal cabin 680 includes multiple sections, including a main cabin 682 having passenger seats 683, and an aft section 685 behind the main cabin 682. It is to be understood that the internal cabin 680 may include more or less sections than shown.

The internal cabin 680 may include a single aisle 684 that leads to the aft section 685. The single aisle 684 may extend through the center of the internal cabin 680 that leads to the aft section 685. For example, the single aisle 684 may be coaxially aligned with a central longitudinal plane of the internal cabin 680.

One or more enclosed spaces 102, such as lavatories, may be located within the internal cabin 680. UV light sanitizing systems may be used to sanitize structures within the lavatories 102, such as described above.

As described herein, embodiments of the present disclosure provide systems and methods that indicate that surfaces within an enclosed space (such as a lavatory) have been sanitized and are clean. Further, embodiments of the present disclosure provide systems and methods that allow individuals to rest assured that surfaces within a lavatory, for example, are clean and sanitary.

While various spatial and directional terms, such as top, bottom, lower, mid, lateral, horizontal, vertical, front and the like may be used to describe embodiments of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A cleanliness indication system that is configured to indicate that at least one surface within a lavatory is clean, the cleanliness indication system comprising:
a photoluminescent indicator that forms at least a portion of the at least one surface within the lavatory, wherein the photoluminescent indicator is configured to be exposed to ultraviolet (UV) light during a UV light sanitizing cycle, wherein the photoluminescent indicator emits light due to exposure to the UV light, and wherein the photoluminescent indicator indicates that the at least one surface within the lavatory is clean by emitting the light due to exposure to the UV light.

2. The cleanliness indication system of claim 1, wherein the photoluminescent indicator emits a visible light after being exposed to a threshold level of UV light energy.

3. The cleanliness indication system of claim 1, wherein the photoluminescent indicator does not emit the light in the absence of being exposed to the UV light.

4. The cleanliness indicator system of claim 1, further comprising a transparent cover positioned over the photoluminescent indicator.

5. The cleanliness indicator system of claim 1, further comprising a light filter positioned over the photoluminescent indicator.

6. The cleanliness indicator system of claim 1, wherein the photoluminescent indicator comprises a strip or block of photoluminescent material having a particular shape.

7. The cleanliness indicator system of claim 1, wherein the photoluminescent indicator is formed as text.

8. The cleanliness indicator system of claim 1, wherein the photoluminescent indicator is formed as a graphic.

9. The cleanliness indication system of claim 1, wherein the photoluminescent indicator forms an entirety of the surface of the component.

10. The cleanliness indication system of claim 1, wherein the at least one surface within the lavatory is at least one surface of a floor, a toilet, or a sink of the lavatory.

11. A cleanliness indication method that is configured to indicate that at least one surface within a lavatory is clean, the cleanliness indication method comprising:
forming at least a portion of the at least one surface within the lavatory with a photoluminescent indicator;
exposing the photoluminescent indicator to ultraviolet (UV) light during a UV light sanitizing cycle;
emitting light from the photoluminescent indicator due to the exposing; and
indicating that the at least one surface within the lavatory is clean by the emitting.

12. The cleanliness indication method of claim 11, wherein the emitting lasts for a predefined period of time after the exposing.

13. The cleanliness indicator method of claim 11, further comprising positioning a transparent cover over the photoluminescent indicator.

14. The cleanliness indicator method of claim 11, further comprising positioning a light filter over the photoluminescent indicator.

15. The cleanliness indicator method of claim 11, further comprising forming the photoluminescent indicator as a strip or block of photoluminescent material having a particular shape.

16. The cleanliness indicator method of claim 11, further comprising forming the photoluminescent indicator as one or more of text or a graphic.

17. The cleanliness indication method of claim 11, wherein the forming comprises forming an entirety of the surface of the component with the photoluminescent indicator.

18. The cleanliness indication method of claim 11, wherein the at least one surface within the lavatory is at least one surface of a floor, a toilet, or a sink of the lavatory.

19. The cleanliness indication method of claim 11, wherein the photoluminescent indicator does not emit the light in the absence of being exposed to the UV light.

20. A vehicle comprising:
an internal cabin;
a lavatory within the internal cabin, wherein the lavatory comprises a floor that supports a toilet and a sink;
at least on ultraviolet (UV) light source that is configured to emit UV light onto at least one surface of the floor, the toilet, or the sink during a UV light sanitizing cycle;
a cleanliness indication system that is configured to indicate that the at least one surface of the floor, the toilet or the sink is clean, the cleanliness indication system comprising:
at least one photoluminescent indicator on the at least one surface of the floor, the toilet, or the sink, wherein the at least one photoluminescent indicator forms at least a portion of the at least one surface of the floor, the toilet, or the sink, wherein the at least one photoluminescent indicator is exposed to the UV light during the UV light sanitizing cycle, wherein the at least one photoluminescent indicator emits light due to exposure to the UV light, and wherein the at least one photoluminescent indicator indicates that the at least one surface is clean by emitting the light due to exposure to the UV light.

* * * * *